United States Patent
Takagi et al.

(10) Patent No.: US 8,118,804 B2
(45) Date of Patent: Feb. 21, 2012

(54) CATHETER ASSEMBLY

(75) Inventors: Ayumu Takagi, Fujinomiya (JP);
Hiroyoshi Ise, Fujinomiya (JP); Daisuke Nakashima, Fujinomiya (JP); Tetsuya Fukuoka, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 138 days.

(21) Appl. No.: 12/511,359

(22) Filed: Jul. 29, 2009

(65) Prior Publication Data

US 2010/0030165 A1    Feb. 4, 2010

(30) Foreign Application Priority Data

Jul. 30, 2008  (JP) .................................. 2008-197012

(51) Int. Cl.
*A61M 25/00*    (2006.01)
(52) U.S. Cl. .................. 604/525; 604/523; 604/534
(58) Field of Classification Search .............. 604/95.04, 604/523–527, 532, 534, 158
See application file for complete search history.

(56) References Cited

U.S. PATENT DOCUMENTS

| 7,494,478 B2 | 2/2009 | Itou et al. |
| 2006/0229589 A1 | 10/2006 | Itou et al. |
| 2007/0149927 A1* | 6/2007 | Itou et al. ..................... 604/158 |

FOREIGN PATENT DOCUMENTS

| JP | 2000-255627 A | 9/2000 |
| JP | 2004-357805 A | 12/2004 |
| JP | 2005-553 A | 1/2005 |
| WO | 2005/056100 A1 | 6/2005 |

* cited by examiner

*Primary Examiner* — Kevin C Sirmons
*Assistant Examiner* — Deanna K Hall
(74) *Attorney, Agent, or Firm* — Buchanan Ingersoll & Rooney PC (57) ABSTRACT

A catheter assembly comprises an outer catheter including an outer catheter body and an outer catheter hub at a proximal portion of the outer catheter body; and an inner catheter including an inner catheter body insertable in the outer catheter body, a tip at the distal portion of the inner catheter body which is rich in flexibility, and an inner catheter hub at the proximal portion of the inner catheter body adapted to be coupled to the outer catheter hub. The inner catheter body includes a flexible section connected the tip, a physical property transition section on the proximal side of the flexible section, a first body section on the proximal side of the physical property transition section, a second body section on the proximal side of the first body section, greater than the first body section in flexural rigidity, and having a reinforcing material layer.

11 Claims, 8 Drawing Sheets

CATHETER ASSEMBLY

TECHNOLOGICAL FIELD

The disclosure here generally pertains to a catheter assembly, more particularly to a catheter assembly insertable in a blood vessel of the head and neck.

BACKGROUND DISCUSSION

For therapy of a blood vessels of the head and neck, for example, a treatment catheter (treatment device) inserted into the blood vessel is used. Since the treatment catheter is generally small in diameter, a pushing force (pushability) and torque (for rotation) applied to the catheter from the proximal side are difficult to transmit to the distal side, due to buckling or bending.

In view of this, prior to insertion of the treatment catheter, a guiding catheter is inserted into the carotid artery communicating with a blood vessel of the head or neck where the region to be cured exists. A distal portion of the guiding catheter is engaged with the carotid artery, and the guiding catheter is fixed to be immovable at the position (target site). This fixation is called engagement.

After the guiding catheter is thus engaged, a guide wire and the treatment catheter are inserted into the guiding catheter, the treatment catheter is moved to protrude from the distal end of the guiding catheter, and is inserted into the blood vessel of the head or neck.

Here, since the blood vessel and the carotid artery are weaker to external forces than cardiac blood vessels and are very susceptible to damage, it is desirable for a distal portion of the guiding catheter to be more flexible. When the distal portion of the guiding catheter is insufficient in flexibility, it may injure the blood vessel. Known guiding catheters having distal portions exhibiting desirable flexibility attributes nevertheless are susceptible of shortcomings.

When a proximal portion of the guiding catheter is pushed in the distal direction to thereby move the guiding catheter in the distal direction, its distal portion is likely to be deflected so that the moving distance of the distal portion is shorter than the pushing-in distance of the proximal portion, and the steerability is poor accordingly.

At the time of inserting or drawing the treatment catheter into or out of the indwelling guiding catheter, the distal portion of the guiding catheter may be disengaged from the carotid artery, and the guiding catheter may slip off from the target site.

Meanwhile, catheter assemblies which each include an outer catheter having an outer catheter body and an outer catheter hub and an inner catheter having an inner catheter body capable of being inserted in the outer catheter body and an inner catheter hub are disclosed in International Application Publication No. WO 2005/056100 (hereinafter referred to as Patent Document 1), Japanese Patent Laid-Open No. 2005-553 (hereinafter referred to as Patent Document 2), and Japanese Patent Laid-Open No. 2004-357805 (hereinafter referred to as Patent Document 3). These catheter assemblies are mainly (cardiac) catheter bodies adapted to be inserted in a cardiac blood vessel. Each of the catheter assemblies is inserted into the blood vessel in an assembled condition in which the inner catheter is coupled to (fitted in) the outer catheter (the condition will hereinafter be referred to simply as "the assembled condition").

In the catheter assembly described in Patent Document 1, however, in the assembled condition a distal portion of the inner catheter only protrudes slightly from the distal end of the outer catheter, so that the inner catheter has only the function of preventing damage to the blood vessel from occurring.

In addition, since the inner catheter body does not have any reinforcing material layer, it is poor in steerability. For example, it is difficult to change the direction of the inner catheter by operating the inner catheter alone.

The inner catheter of the catheter assembly described in Patent Document 2 includes a reinforcing material layer which is provided to extend to the distal end of the inner catheter body, and, therefore, the distal portion is insufficient in flexibility.

Further, in the catheter assembly described in Patent Document 3, a distal portion of the inner catheter is higher in rigidity than a distal portion of the outer catheter, and does not protrude from the distal end of the outer catheter (the distal ends of the inner and outer catheters coincide with each other). Therefore, the distal portion of the inner catheter has a poor inhibitive effect on damage to blood vessels.

In addition, since the inner catheter body does not have any reinforcing material layer, it is poor in steerability. For instance, it is difficult to change the direction of the inner catheter through operating the inner catheter singly.

SUMMARY

The disclosed catheter assembly includes an outer catheter comprising an outer catheter body and an outer catheter hub at a proximal portion of the outer catheter body, and an inner catheter comprising: an inner catheter body configured to be inserted in the outer catheter body; a tip at a distal portion of the inner catheter body that is flexible and softer than the distal tip portion of the inner catheter body; and an inner catheter hub at a proximal portion of the inner catheter body and configured to be coupled to the outer catheter hub. The inner catheter body comprises a flexible section having a distal end to which the tip is connected, a physical property transition section located proximally of the flexible section, a first body section located proximally of the physical property transition section, and a second body section located proximally of the first body section. The second body section possesses a flexural rigidity greater than the flexural rigidity of the first body section, and the second body section comprises a reinforcing material layer. The inner catheter body is configured to satisfy the relationships $1<\sigma_{2X}/\sigma_1 \leq 2$ and $1<\sigma_3/\sigma_{2Y} \leq 2$, where $\sigma_1$ [gf] is the flexural rigidity of the flexural section of the inner catheter body in water at a temperature of 37° C., $\sigma_{2X}$ [gf] is the flexural rigidity of a distal portion of the physical property transition section, $\sigma_{2Y}$ [gf] is the flexural rigidity of a proximal portion of the physical property transition section, and $\sigma_3$ [gf] is the flexural rigidity of the first body section. A distal portion of the second body section extends distally beyond a distal-most end of the outer catheter body in an assembled state of the catheter assembly in which the inner catheter body is positioned in the outer catheter body, and the outer catheter hub and the inner catheter hub are coupled to each other, and the flexural rigidity of a distal portion of the outer catheter body is greater than the flexural rigidity of the second body section.

The flexible section preferably possesses a length greater than the length of the physical property transition section.

The physical property transition section can includes a plurality of unit physical property transition sections differing from each other in flexural rigidity, with the flexural rigidity of any one of the unit physical property transition sections on the proximal side of two axially adjacent unit physical property transition sections being greater than the unit physical property transition section on the distal.

The flexural rigidity in water at a temperature of 37° C. of the unit physical property transition section located on the proximal side, of two axially adjacent ones of the unit physical property transition sections, is greater than, and not more than two times, the flexural rigidity in water at a temperature of 37° C. of the unit physical property transition section located on the distal side.

The first body section has an inner layer and an outer layer, and the second body section has an inner layer and an outer layer, with the reinforcing material layer provided between the inner layer and the outer layer.

A hydrophilic lubricating layer is provided on an outer surface of each of the tip and the inner catheter body.

The hydrophilic lubricating layer is preferably provided at that part of the inner catheter body which protrudes from the distal end of the outer catheter in the assembled state.

The inner catheter has, on the proximal side thereof, a lock (or lock means) which holds a coupled condition of the outer catheter hub and the inner catheter hub.

The flexible section is preferably fabricated of material higher in hardness than the material forming the tip so that the flexible section is higher in flexural rigidity than the soft tip.

The physical property transition section is preferably made of a material higher in hardness than the material constituting the flexible section so that the physical property transition section is higher in flexural rigidity than the flexible section.

The first body section is preferably constituted by a material higher in hardness than the material constituting the physical property transition section so that the first body section is higher in flexural rigidity than the physical property transition section.

The second body section preferably possesses a higher flexural rigidity than the first body section because of the reinforcing material layer provided for the second body section.

The catheter assembly is configured so that with a carotid artery-aorta model including a carotid artery made of polyvinyl chloride and an aorta connected to a proximal end of the carotid artery and made of polyvinyl chloride, the distal end of the outer catheter in the assembled state is located in the aorta at a position spaced 120 mm along the aorta from a branching point of the aorta and the carotid artery, the distal end of the inner catheter in the assembled state is located in the carotid artery and the proximal end of the catheter assembly is pushed a pushing-in distance of 50 mm in the distal direction at a velocity of 100 mm/min, an error represented by ((L1−L2)/L1 100) is not more than 10%, where L1 (50 mm) is the pushing-in distance of the proximal end of the catheter assembly, and L2 is a moving distance of the distal end of the inner catheter.

The difference between the inside diameter of the outer catheter body and the outside diameter of the inner catheter body is preferably 0.1 mm to 0.2 mm.

The inside diameter of the inner catheter body is preferably constant along the longitudinal direction of the inner catheter body.

The inside diameter of the outer catheter body is preferably constant along the longitudinal direction of the outer catheter body.

Preferably, the flexural rigidity of a distal portion of the outer catheter body is lower than the flexural rigidity on the proximal side thereof.

According to another aspect, a catheter assembly comprises an outer catheter comprised of an outer catheter body and an outer catheter hub at a proximal portion of the outer catheter body, and an inner catheter comprised of: an inner catheter body possessing an outer circumference configured to allow the inner catheter body to be positioned inside the outer catheter body; a tip at a distal-most portion of the inner catheter body, the tip being softer that the distal portion of the inner catheter body; and an inner catheter hub at a proximal portion of the inner catheter body and configured to be coupled to the outer catheter hub in a coupled condition by way of a lock which holds the inner and outer catheter bodies in a coupled condition. The inner catheter body comprises a flexible section having a distal end to which is fixed the tip, a physical property transition section on a proximal side of the flexible section, a first body section on the proximal side of the physical property transition section, and a second body section on the proximal side of the first body section. The second body section possesses a flexural rigidity greater than the flexural rigidity of the first body section, the second body section comprises a reinforcing material layer embedded in material of which the second body section is made, and the reinforcing material layer is made of a material different from the material of which the second body section is made. The catheter assembly is configured to satisfy the relationships $1<\sigma_{2X}/\sigma_1 \leq 2$ and $1<\sigma_3/\sigma_{2Y} \leq 2$, where $\sigma_1$ [gf] is the flexural rigidity of the flexural section of the inner catheter body in water at a temperature of 37° C., $\sigma_{2X}$ [gf] is the flexural rigidity of a distal portion of the physical property transition section, $\sigma_{2Y}$ [gf] is the flexural rigidity of a proximal portion of the physical property transition section, and $\sigma_3$ [gf] is the flexural rigidity of the first body section. The inner catheter and the outer catheter each possess a length such that with the inner catheter positioned inside the outer catheter and the outer catheter hub and the inner catheter hub coupled to each other in the coupled condition by the lock, the distal portion of the second body section protrudes distally beyond a distal-most end of the outer catheter body. The flexural rigidity of the distal portion of the outer catheter body is higher than the flexural rigidity of the second body section.

In the catheter assembly disclosed here, the inner catheter body has the flexible section having a distal end to which is connected the soft tip which is rich in flexibility. The inner catheter body also has, on the proximal side of the flexible section, the second body section sequentially having the physical property transition section, the first body section and the reinforcing material layer, a distal portion of the second body section protrudes from the distal end of the outer catheter body in the assembled condition, and the variations in flexural rigidity at the boundaries between the sections in the assembled condition are small. This helps ensure that kinking at the time of insertion of the catheter assembly into a living body can be prevented.

In addition, a force for pushing the catheter assembly from the proximal side toward the distal side (pushability) and a torque are easily transmitted to the distal side, so that steerability is good. Besides, injury of the inner wall of a blood vessel by the catheter assembly at the time of insertion into a living body is obviated, so that safety is relatively high.

Accordingly, the catheter assembly can be inserted into a target region relatively safely and assuredly through a relatively simple operation.

In addition, the flexural rigidity of a distal portion of the outer catheter body is comparatively high, which helps ensure that the outer catheter indwelling in a target site can be reliably fixed (held) in the target site.

DETAILED DESCRIPTION

Figure 2:
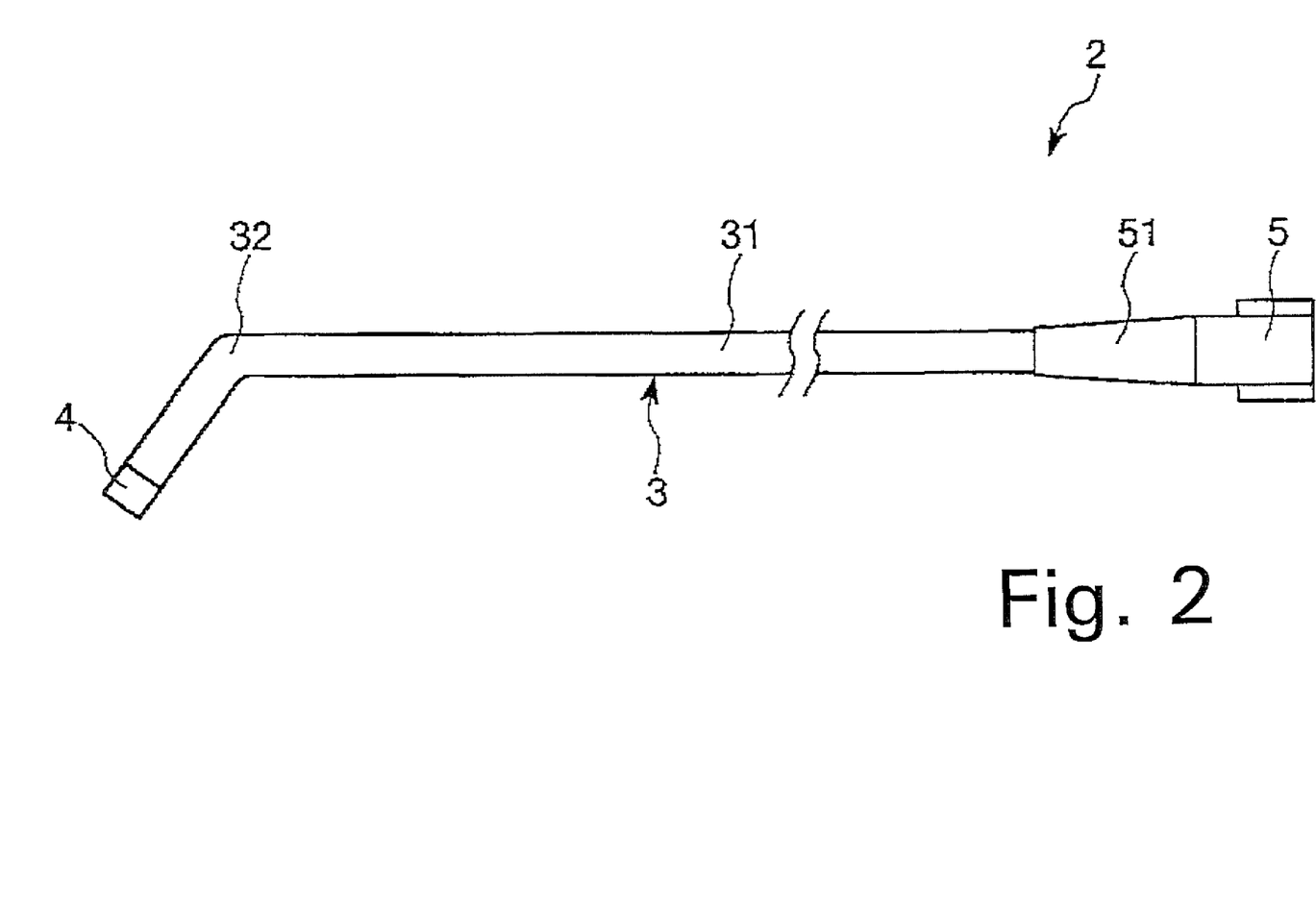
FIG. 2 is a plan view of the outer catheter of the catheter assembly shown in FIG. 1.
Figure 3:
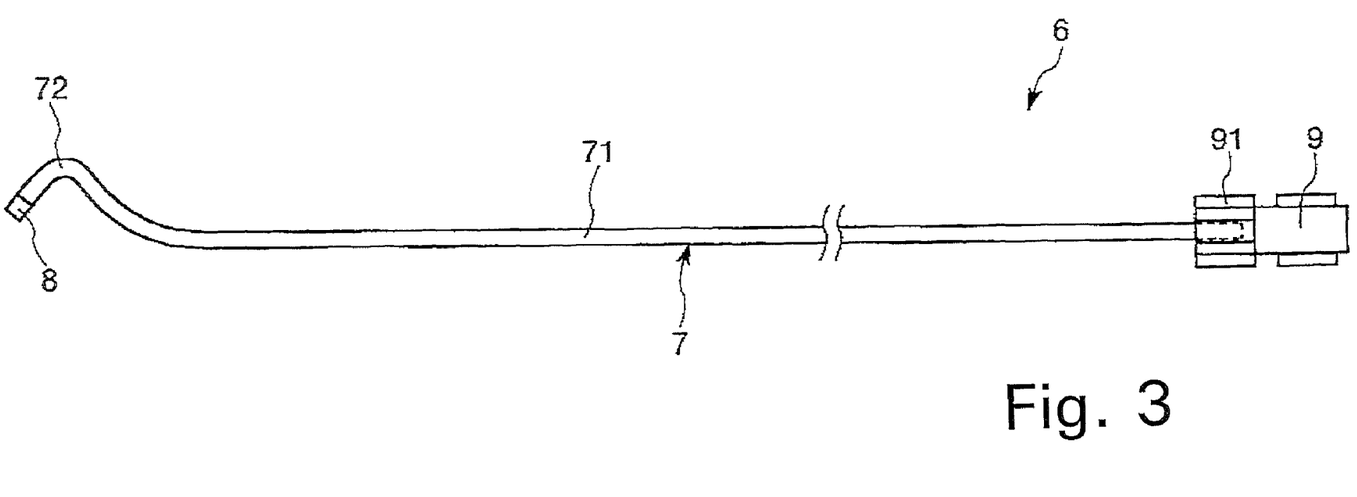
FIG. 3 is a plan view of the inner catheter of the catheter assembly shown in FIG. 1.
Figure 4:
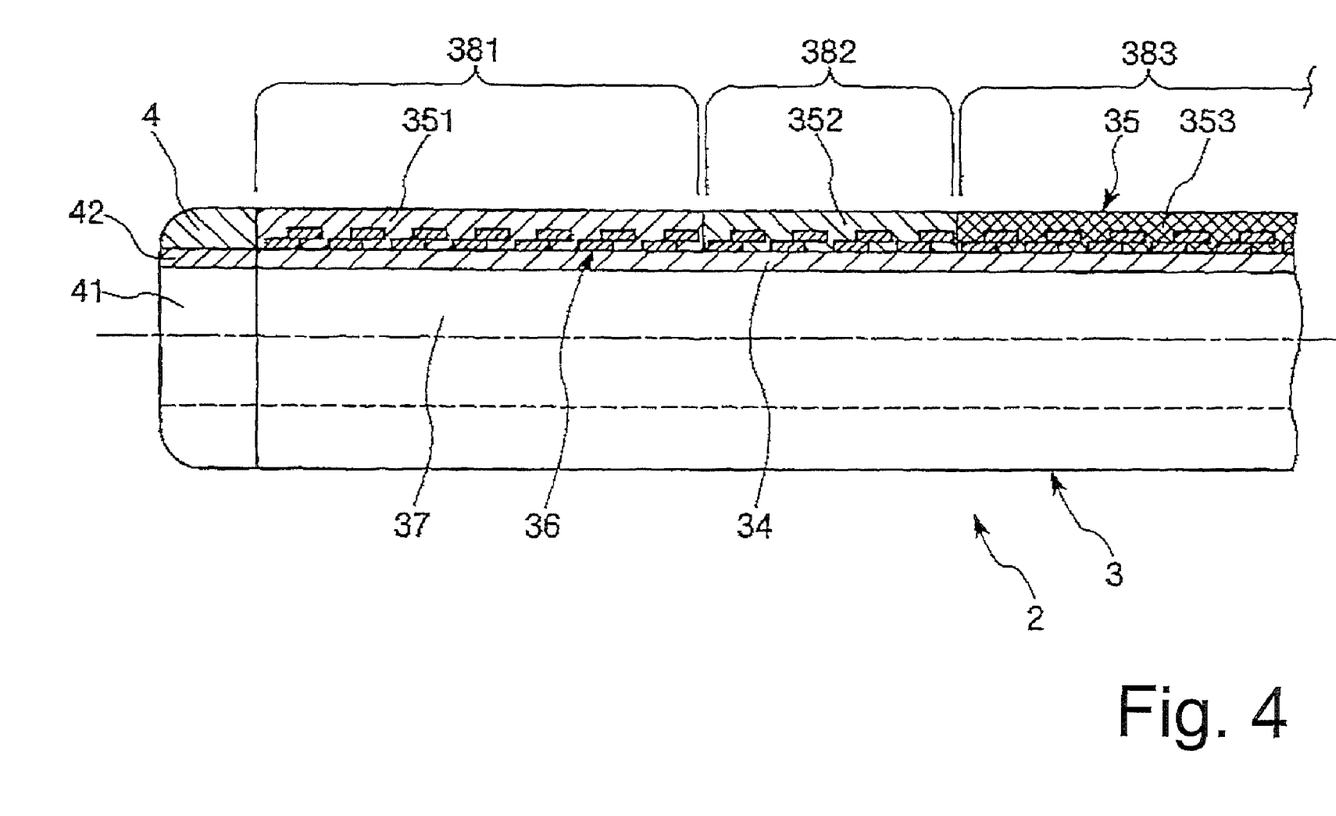
FIG. 4 is a longitudinal cross-sectional view of the distal side of the outer catheter of the catheter assembly shown in FIG. 1.
Figure 5:
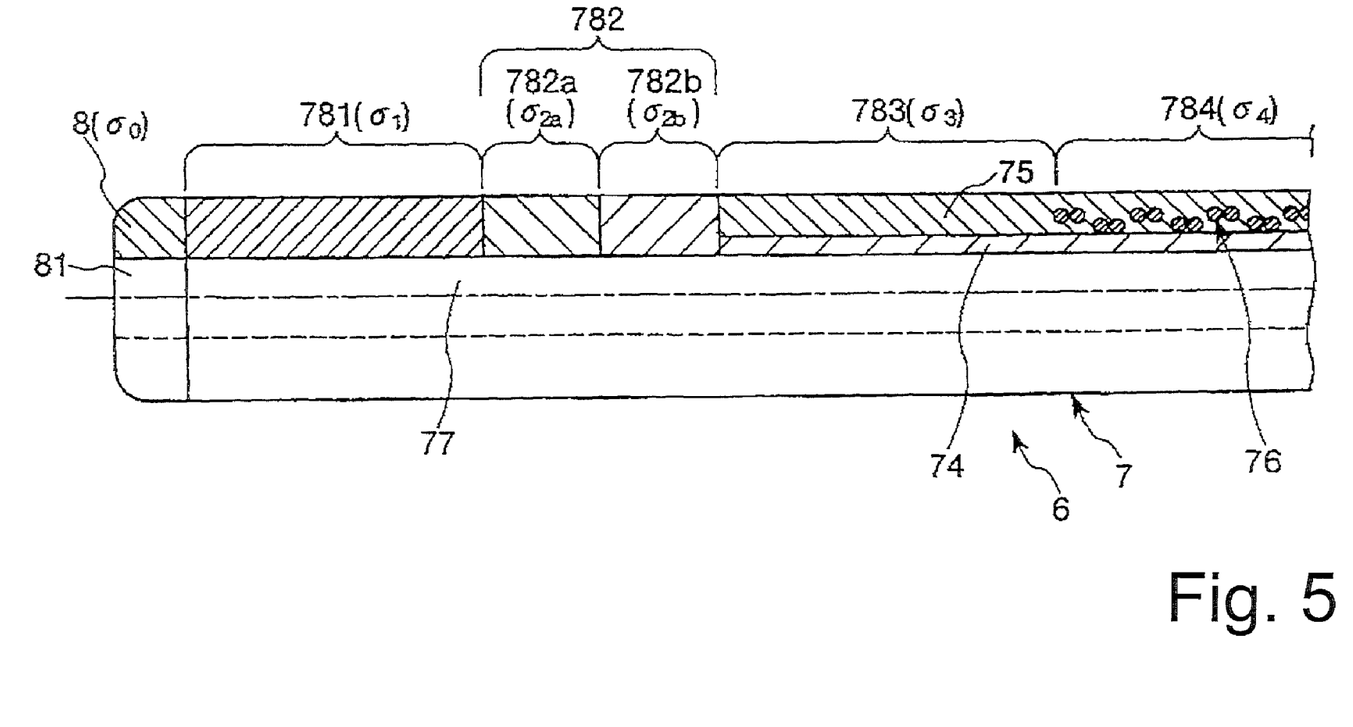
FIG. 5 is a longitudinal cross-sectional view of the distal side of the inner catheter of the catheter assembly shown in FIG. 1.
Figure 6:
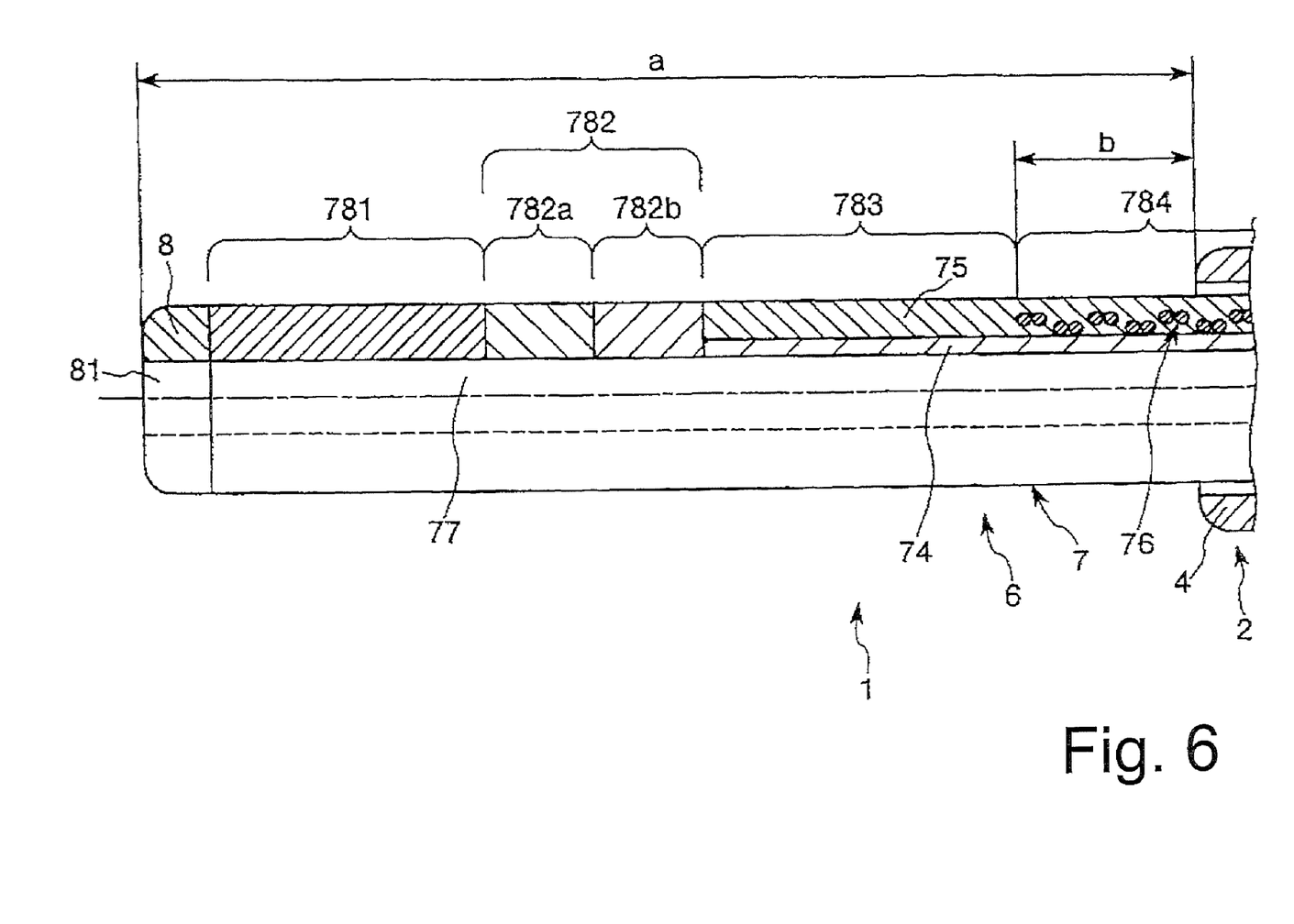
FIG. 6 is a longitudinal cross-sectional view of the distal side of the catheter assembly shown in FIG. 1 in the assembled condition.

In the description which follows, the right side in FIGS. 1-6 is referred to as the "proximal end (proximal side)," the left side is referred to as the "distal end," the side closer to the proximal end is referred to as the "proximal," and the side farther from the proximal end is referred to as the "distal" in the following description. In addition, the upper side in FIGS. 7 and 8 will be referred to as the "proximal end (proximal side)" and the lower side is referred to as the "distal end" in the following description. FIGS. 4-6 illustrate the condition in which the outer catheter and the inner catheter are set rectilinear for easy understanding.

The catheter assembly 1 disclosed here and illustrated in the drawing figures is a catheter assembly adapted to be inserted in a blood vessel of the head and neck. The outer catheter 2 of the catheter assembly is used as a guiding catheter by which a treatment catheter is guided to a region where therapy is conducted.

Figure 1:
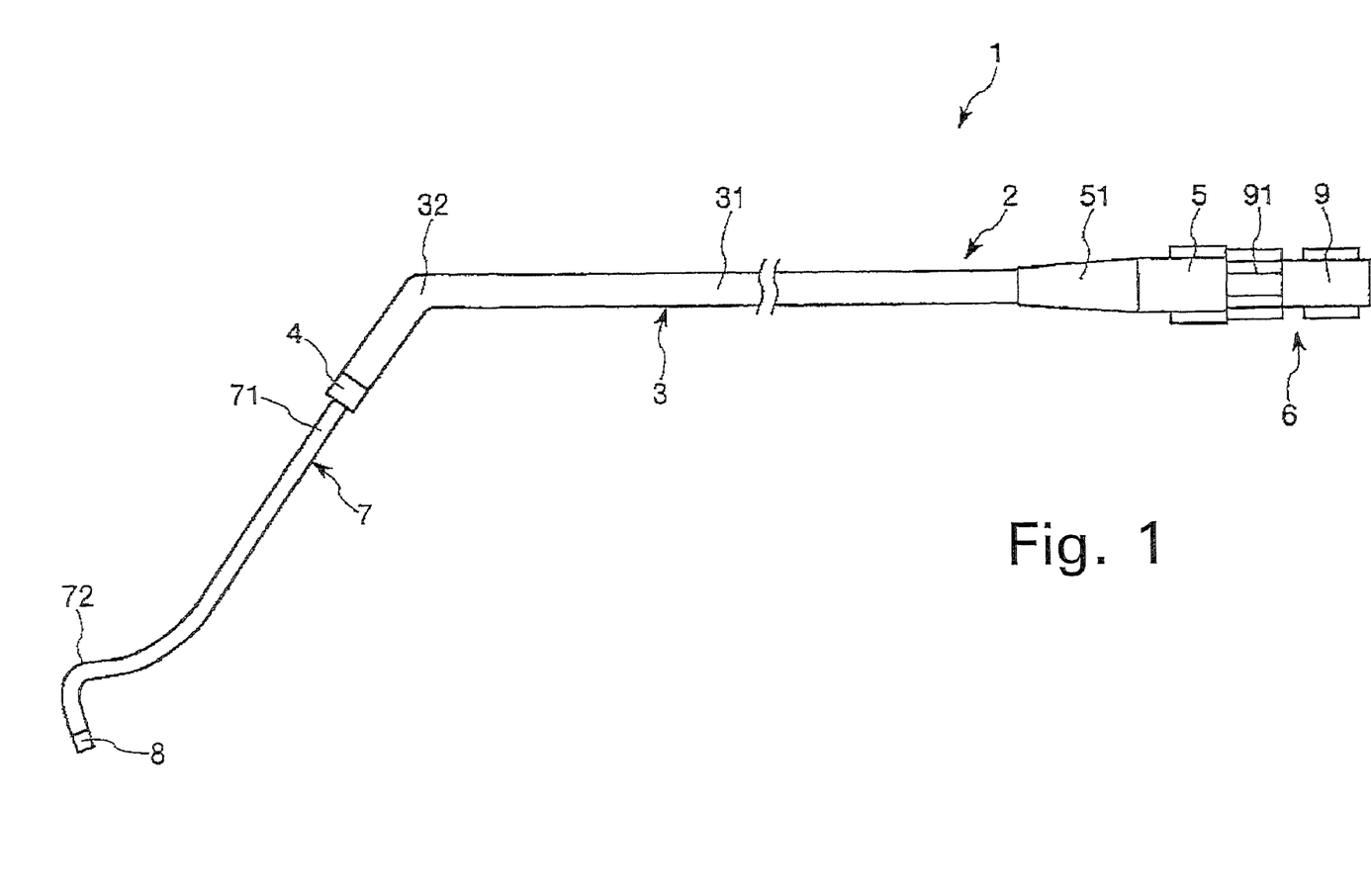
FIG. 1 is a plan view of an embodiment of the catheter assembly in the assembled condition according disclosed here.

As shown in FIG. 1, the catheter assembly 1 is comprised of the outer catheter 2 and the inner catheter 6. FIG. 2 shows that the outer catheter 2 includes an outer catheter body 3, a soft tip 4 at a distal portion of the outer catheter body 3 which is rich in flexibility, and a hub (outer catheter hub) 5 at a proximal portion of the outer catheter body 3. The soft tip 4 is softer than the distal portion of the outer catheter body 3.

As shown in FIG. 3, the inner catheter 6 includes an inner catheter body 7 adapted to be inserted in the outer catheter body 3, a soft tip 8 at the distal portion of the inner catheter body 7 which is rich in flexibility, and a hub (inner catheter hub) 9 provided at a proximal portion of the inner catheter body 7 and configured to be coupled to the hub 5. The soft tip 8 is softer than the distal portion of the inner catheter body 7.

The condition where the inner catheter body 7 is positioned in the outer catheter body 3 and the hub 9 is coupled to (fitted in) the hub 5 as shown in FIG. 1 is the condition where the outer catheter 2 and the inner catheter 6 are assembled together (hereinafter referred to simply as "the assembled condition"). In the assembled condition, the distal side of the inner catheter body 7 protrudes from the distal end of the soft tip 4 of the outer catheter 2.

Additional details and features of the outer catheter 2 will be described initially. The outer catheter body 3 of the outer catheter 2 is comprised of a flexible tube (tubular body), and is provided with a centrally located lumen 37 extending over the whole length of the outer catheter body 3. The lumen 37 opens at the distal end of the soft tip 4. In other words, the soft tip 4 is provided with a tip opening 41 communicating with the lumen 37.

As shown in FIG. 4, the tube constituting the outer catheter body 3 is a laminate body in which are laminated three layers, an inner layer 34, an outer layer 35 and a reinforcing material layer 36 located between the inner layer 34 and the outer layer 35.

The outer layer 35 has a first region 351, a second region 352 located (provided) on the proximal side of the first region 351, and a third region 353 located on the proximal side of the second region 352.

Specifically, the outer catheter body 3 has a first part (distal portion) 381, a second part 382 located (provided) on the proximal side of the first part 381, and a third part 383 located on the proximal side of the second part 382. The first part 381, the second part 382 and the third part 383 correspond respectively to the first region 351, the second region 352 and the third region 353.

The second region 352 is richer in flexibility than the third region 353, and the first region 351 is more flexible than the second region 352. In other words, the flexural rigidity (stress in flexure) of the second part 382 is greater than the flexural rigidity of the first part 381, and the flexural rigidity of the third part 383 is greater than the flexural rigidity of the second part 382. This configuration helps ensure that the outer catheter body 3 is gradually increased in flexibility along the distal direction and that at the time of insertion into a blood vessel, the outer catheter body 3 can be inserted into the blood vessel more safely while sufficiently securing pushability and performance of transmission of torque to the distal side.

In addition, the flexural rigidity of the first part 381 is greater than the flexural rigidity of a second body section 784. The second body section 784 is the part of the inner catheter 7 that is highest in flexural rigidity as discussed more fully below. Specifically, the flexural rigidity of the first part 381 is comparatively high, which helps ensure that at the time of inserting or drawing the treatment catheter into and out of the outer catheter 2 indwelling in a target site, disengagement of the outer catheter body 3 from a carotid artery and the attendant slip-off of the outer catheter 2 from the target site can be inhibited or prevented from occurring, and the outer catheter 2 can be reliably fixed (held) in the target site.

Examples of each of materials for forming the first region 351, the second region 352 and the third region 353 include various thermoplastic elastomers based on styrene, polyolefin, polyurethane, polyester, polyamide, polybutadiene, trans-polyisoprene, fluoro-rubber or chlorinated polyethylene, which may be used either singly or in combination of two or more thereof (polymer alloys, polymer blends, laminates, etc.).

The material constituting the inner layer 34 is not particularly limited. However, that part of the inner layer 34 which makes contact with at least the inner catheter body 7 at the time of inserting the inner catheter body 7 into the lumen 37 (into the outer catheter body 3) is desirably composed of a low-friction material. This ensures that the inner catheter body 7 can be moved in the longitudinal direction or rotated in relation to the outer catheter body 3 with a smaller sliding resistance, which contributes to enhancement of steerability.

Examples of the low-friction material include various resin materials such as polyamides, polyether polyamides, polyester polyamides, polyesters (polyethylene terephthalate, polybutylene terephthalate, polyethylene naphthalate, etc.), polyurethane, flexible polyvinyl chloride, ABS resin, AS resin, fluoro-resins such as polytetrafluoroethylene (PTFE), etc.

The reinforcing material layer 36 comprises a reinforcing material such as a single or plurality of reinforcing wires or filaments (filamentous members or elements) for reinforcing the outer catheter body 3. Examples of the reinforcing material include reinforcing wires or filaments formed into a spiral or netted shape. The reinforcing wires or filaments are composed of a metal, a hard resin or the like. Specific examples of the reinforcing material include those obtained by crushing a stainless steel wire into a flat shape (belt-like shape) and forming it into a spiral shape, a braided shape (braid) or the like so that the thickness thereof in the radial direction of the outer catheter body 3 will be small.

The reinforcing material layer 36 helps impart sufficient rigidity and strength without increasing the wall thickness of the outer catheter body 3, in other words while securing a comparatively large inside diameter (the diameter of the lumen 37). As a result, it is possible to obtain an outer catheter 2 in which an inner catheter body 7 with a comparatively large outside diameter can be inserted, which is excellent in pushability and torque transmission performance and is less susceptible to kinking or crushing.

In addition, the outer catheter body 3 preferably has an inside diameter which is constant along the longitudinal direction thereof. This helps ensure that an inner catheter body with a comparatively large outside diameter can be inserted in the outer catheter body 3.

The inside diameter of the outer catheter body 3 is not particularly limited, but is preferably about 1.2 to 2.4 mm, more preferably about 1.45 to 1.90 mm. The outside diameter of the outer catheter body 3 is also not particularly limited, though is preferably about 1.3 to 2.7 mm (a size of 4 to 8 Fr), more preferably about 1.6 to 2.2 mm (a size of 5 to 6 Fr).

Factors such as the number of layers constituting the outer catheter body 3, the material(s) constituting the layer(s), and the presence/absence of the reinforcing material layer may differ along the longitudinal extent of the outer catheter body 3. For instance, at the part on the distal side of the outer catheter body 3 (for example, the first part 381), the number of layers may be reduced, a more flexible material may be used, or the reinforcing material may be absent only at this part, for securing higher flexibility.

Since the insertion of the catheter assembly 1 into a living body is carried out while checking its position under radioscopic observation, a radiopaque material (radiopaque agent) is preferably blended in the material constituting the outer layer 35. Examples of the material which can be used as the radiopaque material include barium sulfate, bismuth oxide, and tungsten. The proportion in which the radiopaque material is blended into the material constituting the outer layer 35 is preferably 30 to 80 wt. %.

In addition, the configuration in which such a radiopaque material is present over the whole length of the outer catheter body 3 is not required. Configurations may be adopted in which the radiopaque material is present only at a part of the outer catheter body 3, for instance at the first part 381 or at a part including the first part 381, or is present only at the soft tip 4.

In addition, the configuration in which that part of the inner layer 34 which makes contact with the inner catheter body 7 is composed of a low-friction material as mentioned above is not limitative. For example, the inner layer 34 may be wholly composed of a low-friction material.

The outer catheter body 3 has a rectilinear portion 31 which extends rectilinearly, and a deformed portion 32 which has a desired bent or curved shape, in this order from the proximal side along the longitudinal direction of the outer catheter body 3. The deformed portion 32 preferably has a shape facilitating the engagement of the outer catheter body 3 with a carotid artery (engaging operation), or such a shape that the condition where the outer catheter body 3 is engaged with the carotid artery (engagement) can be maintained more securely.

In addition, the soft tip 4 is further attached to the distal end of the outer catheter body 3, specifically, the distal end of the first part 381. The soft tip 4 is composed of a material which is rich in flexibility, and its distal end is preferably rounded in shape. With such a soft tip 4 provided, the outer catheter body 3 can be moved relatively smoothly and safely even in curved, bent or branched blood vessels.

Examples of the material constituting the soft tip 4 include various rubber materials such as natural rubber, isoprene rubber, butadiene rubber, chloroprene rubber, silicone rubber, fluoro-rubber, styrene-butadiene rubber, etc., and various thermoplastic elastomers based on styrene, polyolefin, polyurethane, polyester, polyamide, polybutadiene, trans-polyisoprene, fluoro-rubber, or chlorinated polyethylene.

Besides, a radiopaque material (radiopaque agent) as above-mentioned may be blended in the material constituting the soft tip 4. The length of the soft tip 4 is not particularly limited; usually, the length is preferably about 0.5 to 3 mm, and more preferably about 1 to 2 mm.

In addition, an inner layer 42 is provided at the inner peripheral surface (inside surface) of the soft tip 4. The material constituting the inner layer 42 is not limited to a particular material. The inner layer 42 is preferably composed of a low-friction material, like the inner layer 34. Examples of low-friction materials which can be used for the inner layer 42 include the same low-friction materials as those for forming the inner layer 34. It is possible to use a soft tip in which the inner layer 42 is not present at all or in which the inner layer 42 is present only partly (locally).

The hub 5 is attached (fixed) to the proximal end of the outer catheter body 3. The hub 5 possesses an inner cavity communicating with the lumen 37. The inner cavity has an inside diameter approximately equal to the inside diameter of the lumen 37, and is continuous with the inside surface of the proximal portion of the lumen 37, without any step or the like between the inside diameter of the lumen 37 and the inside surface of the proximal portion of the lumen 37.

Through the hub 5, a long body (filamentous body) such as, for example, a guide wire, treatment catheters (for example, balloon catheter, micro-catheter, stent, dilation catheter, thrombectomy catheter, embolus introducing catheter), an endoscope, an ultrasonic probe, a temperature sensor, etc. can be inserted or evulsed, and various liquids such as a radiopaque agent, a liquid drug, physiological saline, etc. can be injected. In addition, the hub 5 can be connected to other implements at the time of blood pressure measurement, for example.

A covering member (anti-kinking protector) 51 having a reinforcing function and formed from an elastic material is provided at the part where the outer catheter body 3 and the hub 5 are connected to each other. This makes it possible to inhibit or prevent kinking from occurring in the vicinity of that part.

Details and features of the inner catheter 6 will now be described. The inner catheter body 7 is composed of a flexible tube (tubular body) having a centrally located lumen 77 extending over the whole length of the inner catheter body 7. The lumen 77 is opened at the distal end of the soft tip 8. In other words, the soft tip 8 is provided with a tip opening 81 communicating with the lumen 77.

As shown in FIG. 5, the tube constituting the inner catheter body 7 includes a flexible section 781 having a distal end to which is connected or fixed the soft tip 8, a physical property transition section 782 located (provided) on the proximal side of the flexible section 781, a first body section 783 located on the proximal side of the physical property transition section 782, and a second body section 784 located on the proximal side of the first body section 783. In the illustrated embodiment, the flexible section 781, the physical property transition section 782, the first body section 783 and the second body section 784 do not axially overlap one another. These sections are different from each other in flexural rigidity. Specifically, the section located on the more proximal side has a higher flexural rigidity. That is, each successive section in the proximal direction has a higher flexural rigidity than the preceding section so that section 782 has a higher flexural rigidity than section 781, section 783 has a higher flexural rigidity than section 782, and section 784 has a higher flexural rigidity than section 783.

The physical property transition section 782 is composed of a plurality of unit physical property transition sections differing from each other in flexural rigidity. In this embodiment, the plurality of unit physical property transition sections includes a first unit physical property transition section 782a and a second unit physical property transition section 782b located on the proximal side of the first unit physical property transition section 782a. The unit physical property transition sections located on the more proximal side is higher in flexural rigidity. Specifically, the flexural rigidity of the second unit physical property transition section 782b located on the proximal side is higher than the flexural rigidity of the first unit physical property transition section 782a located on the distal side. With more than two unit physical property transition sections, the same relationship in flexural rigidity applies (i.e., as between two axially adjoining unit physical property transition sections, the one on the proximal side possesses a great flexural rigidity).

This configuration helps ensure that the inner catheter body 7 is gradually increased in flexibility along the distal direction, and that at the time of insertion into a blood vessel, the inner catheter body 7 can be inserted more safely for the blood vessel while sufficiently securing pushability and performance of transmission of torque toward the distal side. In addition, insertion into a blood vessel can be performed under a relatively small resistance.

The first body section 783 is composed of a laminate body in which two layers, i.e., an inner layer 74 and an outer layer 75 are laminated. The inner layer 74 and the outer layer 75 are made of different material compositions.

In addition, the second body section 784 is a laminate body comprising three layers which are laminated, i.e., an inner layer 74, an outer layer 75, and a reinforcing material layer 76 located between the inner layer 74 and the outer layer 75. The length of the second body section 784 occupies most, for example about 80 to 95% (preferably, about 85 to 90%), of the whole length of the inner catheter body 7. Therefore, the presence of the reinforcing material layer 76 in the second body section 784 helps ensure that a sufficient torque transmission performance is secured, the inner catheter body 7 can be relatively easily rotated (turned) in the circumferential direction while gripping the hub 9, and the direction of the inner catheter body 7 can be changed relatively easily, whereby steerability is enhanced.

The methods or mechanisms for adjusting (the methods for setting) the flexural rigidities of the sections are not particularly limited. It is preferable, however, to fabricate the flexible section 781 with a material higher in hardness (Shore hardness) than the material constituting the soft tip 8 so that the flexible section 781 will be higher in flexural rigidity than the soft tip 8.

In addition, the first unit physical property transition section 782a is preferably composed of a material higher in hardness than the material constituting the flexible section 781 so that the first unit physical property transition section 782a will be higher in flexural rigidity than the flexible section 781.

The second unit physical property transition section 782b is preferably composed of a material higher in hardness than the material constituting the first unit physical property transition section 782a so that the second unit physical property transition section 782b will be higher in flexural rigidity than the first unit physical property transition section 782a.

In addition, the first body section 783 is preferably composed of a material higher in hardness than the material constituting the second unit physical property transition section 782b so that the first body section 783 will be higher in flexural rigidity than the second unit physical property transition section 782b.

Further, the second body section 784 is preferably higher in flexural rigidity than the first body section 783 by virtue of the presence of the reinforcing material layer 76.

Examples of the materials constituting the flexible section 781, the first unit physical property transition section 782a, the second unit physical property transition section 782b, the inner layer 74 and the outer layer 75 include various thermoplastic elastomers based on styrene, polyolefin, polyurethane, polyester, polyamide, polybutadiene, trans-polyisoprene, fluoro-rubber, or chlorinated polyethylene, which may be used either singly or in combination of two or more thereof (polymer alloys, polymer blends, laminates, etc.).

In versions of the catheter involving the use of the same resin material, the hardness of the resin material can be controlled (varied as described above) by regulating (changing) the ratio between hard segments and soft segments constituting the resin material.

The lengths of the flexible section 781, the first unit physical property transition section 782a, the second unit physical property transition section 782b, the first body section 783 and the second body section 784 are not particularly limited. Preferably, the length of the flexible section 781 is greater than the respective lengths of the first unit physical property transition section 782a and the second unit physical property transition section 782b, and more preferably greater than the sum of the length of the first unit physical property transition section 782a and the length of the second unit physical property transition section 782b. Specifically, the length of the flexible section 781 is preferably about 30 to 120 mm, more preferably about 45 to 80 mm. This setting helps enable extremely safe insertion into a blood vessel.

The reinforcing material layer 76 comprises a reinforcing material composed of a single or a plurality of reinforcing wires or filaments (filamentous bodies) for reinforcing the second body section 784. Examples of the reinforcing material include reinforcing wires or filaments helically wound or other formed into a spiral or netted shape. The reinforcing wires or filaments are composed of a metal, a hard resin or the like. Specific examples of the reinforcing material include those obtained by crushing, or not crushing, a stainless steel wire into a flat shape (belt-like shape) and forming the crushed wire, or forming the non-crushed round-sectional wire, into a spiral shape, a braided shape (braid) or the like so that the thickness thereof in the radial direction of the second body section 784 will be relatively small.

With such a reinforcing material layer 76 provided, sufficient rigidity and strength can be secured, without increasing the wall thickness of the second body section 784, in other words while securing a comparatively large inside diameter (diameter of the lumen 77). As a result, it is possible to obtain an inner catheter 6 in which a treatment catheter with a comparatively large outside diameter can be inserted, which is excellent in pushability and torque transmission performance and is less susceptible to kinking or crushing.

In addition, let the flexural rigidity of the soft tip 4 in water at a temperature of 37° C. be $\sigma_0$ [gf], and in the same condition, let the flexural rigidity of the flexible section 781 of the inner catheter body 7 be $\sigma_1$ [gf], let the flexural rigidity of the first unit physical property transition section 782a be $\sigma_{2a}$ [gf] (corresponding to the flexural rigidity $\sigma_{2X}$ [gf] of the distal portion of the physical property transition section 782), let the flexural rigidity of the second unit physical property transition section 782b be $\sigma_{2b}$ [gf] (corresponding to the flexural rigidity $\sigma_{2Y}$ [gf] of the proximal portion of the physical property transition section 782), let the flexural rigidity of the first body section 783 be $\sigma_3$ [gf], and let the flexural rigidity of the second body section 784 be $\sigma_4$ [gf], then a configuration is adopted to satisfy the following relationships $1<\sigma_{2a}/\sigma_1 \leq 2$, $1<\sigma_{2b}/\sigma_{2a} \leq 2$, and $1<\sigma_3/\sigma_{2b} \leq 2$; ($1<\sigma_{2Y}/\sigma_{2X} \leq 2$).

If the ratios $\sigma_{2a}/\sigma_1$, $\sigma_{2b}/\sigma_{2a}$, and $\sigma_3/\sigma_{2b}$ (and $\sigma_{2Y}/\sigma_{2X}$) exceed the above-mentioned upper limits, the differences in physical property are too large, so that at the time of inserting the catheter assembly 1 into a blood vessel, pushability may be insufficient and/or kinking may occur. Besides, the resistance felt at the time of insertion into a blood vessel will be relatively high. On the other hand, if the ratios $\sigma_{2a}/\sigma_1$, $\sigma_{2b}/\sigma_{2a}$, and $\sigma_3/\sigma_{2b}$ (and $\sigma_{2Y}/\sigma_{2X}$) are below the above-mentioned lower limits ($\leq 1$), the catheter assembly 1 cannot be pushed into a blood vessel.

It is particularly preferable to satisfy the relationships $1.3 \leq \sigma_{2a}/\sigma_1 \leq 2.0$, $1.3 \leq \sigma_{2b}/\sigma_{2a} \leq 2.0$, and $1.3 \leq \sigma_3/\sigma_{2b} \leq 2.0$. More preferably, the following relationships should be satisfied: $1.3 \leq \sigma_{2a}/\sigma_1 \leq 1.8$, $1.3 \leq \sigma_{2b}/\sigma_{2a} \leq 1.8$, and $1.3 \leq \sigma_3/\sigma_{2b} \leq 1.8$.

In addition, the flexural rigidity $\sigma_0$ of the soft tip 4 is preferably about 0.5 to 3 gf, more preferably about 1 to 2.5 gf. The flexural rigidity $\sigma_1$ of the flexible section 781 is preferably about 1 to 5 gf, more preferably about 2 to 4 gf. Further, the flexural rigidity $\sigma_{2a}$ of the first unit physical property transition section 782a is preferably about 2 to 8 gf, more preferably about 3 to 6 gf. In addition, the flexural rigidity $\sigma_{2b}$ of the second unit physical property transition section 782b is preferably about 3 to 9 gf, more preferably about 4 to 8 gf. Besides, the flexural rigidity $\sigma_3$ of the first body section 783 is preferably about 4 to 15 gf, more preferably about 8 to 12 gf. Further, the flexural rigidity $\sigma_4$ of the second body section 784 is preferably about 10 to 30 gf, more preferably about 15 to 25 gf.

With the above-mentioned upper limit conditions satisfied, at the time of insertion of the catheter assembly 1 into a blood vessel, a more safe insertion to the blood vessel can be achieved while further enhancing the pushability and performance of transmission of torque to the distal side.

The physical property transition section 782 may not necessarily be divided into a plurality of sections (two sections) as in the illustrated embodiment, and may instead be a single section. In the latter case, let the flexural rigidity of the physical property transition section 782 in water at a temperature of 37° C. be $\sigma_2$ [gf], then a configuration is adopted to satisfy the following relationships $1<\sigma_2/\sigma_1 \leq 2$ and $1<\sigma_3/\sigma_2 \leq 2$ ($\sigma_{2X}=\sigma_{2Y}$), more preferably the following relationships: $1.6 \leq \sigma_2/\sigma_1 \leq 2$ and $1.6 \leq \sigma_3/\sigma_2 \leq 2$.

In addition, the flexural rigidity $\sigma_2$ of the physical property transition section 782 is preferably about 2 to 9 gf, more preferably about 5 to 6 gf.

Incidentally, it is preferable that neither the inner catheter body 7 nor the soft tip 8 is provided with a layer of a low-friction material at the inner peripheral surface (inside surface) thereof. The reason is as follows. Providing such a layer does not produce any favorable effect. However, providing such a layer would increase the flexural rigidity so as to reduce flexibility, and would reduce the inside diameters of the inner catheter body 7 and the soft tip 8.

In addition, the inside diameter of the inner catheter body 7 is preferably constant along the longitudinal direction. This makes it possible to insert a treatment catheter with a comparatively large outside diameter.

The difference between the outside diameter of the inner catheter body 7 and the inside diameter of the outer catheter body 3 is preferably about 0.1 to 0.2 mm. This helps enable the inner catheter body 7 to be smoothly rotated (turned) in the circumferential direction relative to the outer catheter body 3, whereby steerability is enhanced.

The inside diameter of the inner catheter body 7 is not particularly limited, though is preferably about 0.8 to 1.8 mm, more preferably about 0.9 to 1.6 mm. In addition, though the outside diameter of the inner catheter body 7 is not particularly limited, it is preferably about 1.1 to 2.3 mm, more preferably about 1.3 to 2.0 mm.

Factors such as the number of layers constituting the inner catheter body 7 and the materials constituting the layers may differ along the longitudinal direction of the inner catheter body 7.

The insertion of the inner catheter body 7 into a living body is performed while checking its position under radioscopic observation. Therefore, it is preferable that a radiopaque material (radiopaque agent) is blended in the material constituting the outer layer 75. Examples of the radiopaque material include barium sulfate, bismuth oxide, and tungsten. Further, the proportion in which the radiopaque material is blended in the material constituting the outer layer 75 is preferably 30 to 80 wt. %.

In addition, it is not necessary to adopt a construction in which the radiopaque material is present over the whole length of the inner catheter body 7. Configurations may be employed in which the radiopaque material is present only in a part of the inner catheter body 7, for example only in the flexible section 781 or a part including the flexible section 781, or only in the soft tip 8.

The inner catheter body 7 has a rectilinear section 71 which extends rectilinearly, and a deformed section 72 which is deformed so it has a desired bent or curved shape. The rectilinear section 71 and the deformed section 72 are arranged in that order from the proximal side along the longitudinal direction.

Preferably, the deformed section 72 is composed of the flexible section 781 (is included in the flexible section 781).

The soft tip 8 is further connected to the distal end of the inner catheter body 7, specifically the distal end of the flexible section 781. The soft tip 8 is made from a material rich in flexibility, and its distal end is preferably in a rounded shape. This helps ensure that at the time of inserting the inner catheter 6 into a carotid artery, the insertion can be safe to the blood vessel (the inside wall of the carotid artery). In addition, provision of such a soft tip 8 helps enable smooth movement of the inner catheter 8 in curved, bent or branched blood vessels.

Examples of the material constituting the soft tip 8 include various rubber materials such as natural rubber, isoprene rubber, butadiene rubber, chloroprene rubber, silicone rubber, fluoro-rubber, or styrene-butadiene rubber, and various thermoplastic elastomers based on styrene, polyolefin, polyurethane, polyester, polyamide, polybutadiene, trans-polyisoprene, fluoro-rubber, or chlorinated polyethylene.

In addition, a radiopaque material (radiopaque agent) as mentioned above may be blended in the material constituting the soft tip 8.

The length of the soft tip 8 is not particularly limited. Usually though, the length of the soft tip 8 is preferably about 0.5 to 3 mm, more preferably about 1 to 2 mm.

The hub 9 is attached (fixed) to the proximal end of the inner catheter body 7. The hub 9 includes an inner cavity communicating with the lumen 77. The inner cavity has an inside diameter approximately equal to the inside diameter of the lumen 77 so that the inner cavity is continuous with the proximal portion inside surface of the lumen 77, without any step or the like between the inner cavity and the inside surface of the lumen 77.

By way of the hub 9 as described above, a guide wire for example can be inserted or evulsed, and various liquids such as a radiopaque agent, a liquid drug and physiological saline can be injected. In addition, the hub 9 can be connected to other implements at the time of blood pressure measurement, for example.

Though not shown, a covering member (anti-kinking protector) having a reinforcing function and formed from an elastic material may be provided at the part where the inner catheter body 7 and the hub 9 are connected to each other. This makes it possible to inhibit or prevent kinking from occurring at that part.

In addition, the hub 9 is provided with a luer lock connector 91 as a lock or lock means (fixing section) for holding the coupled condition of the hub 9 and the hub 5 of the outer catheter 2. Specifically, the inner catheter 6 is provided with the luer lock connector 91 at a proximal portion (proximal side) thereof. The luer lock connector 91 is provided at its inner peripheral surface (inside surface) with a screw groove for engagement (screw engagement) with a flange of the hub 5 of the outer catheter 2. With the luer lock connector 91 rotated in a predetermined direction, it is fastened so that the coupled condition of the hub 9 and the hub 5 is fixed. This helps ensure that the inner catheter 6 and the outer catheter 2 are fixed to each other so that they will not be rotated or moved relative to each other. This helps the operator (user) to operate (steer) the catheter assembly 1 in the assembled condition through gripping and operating either one of the hubs 9, 5.

The length of the inner catheter body 7 is greater than the length of the outer catheter body 3. In the assembled condition, therefore, a distal portion of the second body section 784, which is the part exhibiting the highest flexural rigidity of the inner catheter body 7, protrudes from the distal end of the first part 381 (the distal end of the outer catheter body 3), which is the part having the lowest flexural rigidity of the outer catheter body 3. Actually, in the assembled condition, the distal portion of the second body section 784 protrudes from the distal end of the outer catheter 2 (the soft tip 4).

This helps ensure that the change in flexural rigidity at the distal end of the outer catheter body 3 (the outer catheter 2) of the catheter assembly 1 in the assembled condition can be reduced, whereby kinking of the catheter assembly 1 can be inhibited or prevented from occurring at the time of insertion into a blood vessel.

The length of the inner catheter body 7 is greater than the length of the outer catheter body 3, preferably by about 100 to 300 mm, more preferably by about 150 to 250 mm.

The protruding length (a) of the inner catheter 6 from the distal end of the outer catheter 2 in the assembled condition shown in FIG. 6 is preferably about 50 to 250 mm, more preferably about 100 to 200 mm.

In addition, the protruding length (b) of the second body section 784 from the distal end of the outer catheter 2 in the assembled condition shown in FIG. 6 is preferably about 3 to 100 mm, more preferably about 5 to 50 mm.

A hydrophilic lubricating layer is preferably provided at the outer peripheral surface (outside surface) of each of the soft tip 8 and the inner catheter body 7. The hydrophilic lubricating layer is preferably provided at that part of the inner catheter body 7 which protrudes from the distal end of the outer catheter 2, specifically, from the distal end of the soft tip 4 in the assembled condition.

Examples of the material (hydrophilic material) constituting the hydrophilic lubricating layer include cellulose polymer substances, polyethylene oxide polymer substances, maleic anhydride polymer substances (e.g., maleic anhydride copolymer such as methyl vinyl ether-maleic anhydride copolymer), acrylamide polymer substances (e.g., polyacrylamide, polyglycidyl methacrylate-dimethylacrylamide (PGMA-DMAA) block copolymer), water-soluble nylon, polyvinyl alcohol, and polyvinylpyrrolidone.

In many cases, such a hydrophilic material exhibits lubricity upon being wetted (absorbing water), to thereby reduce frictional resistance (sliding resistance).

Figure 7:
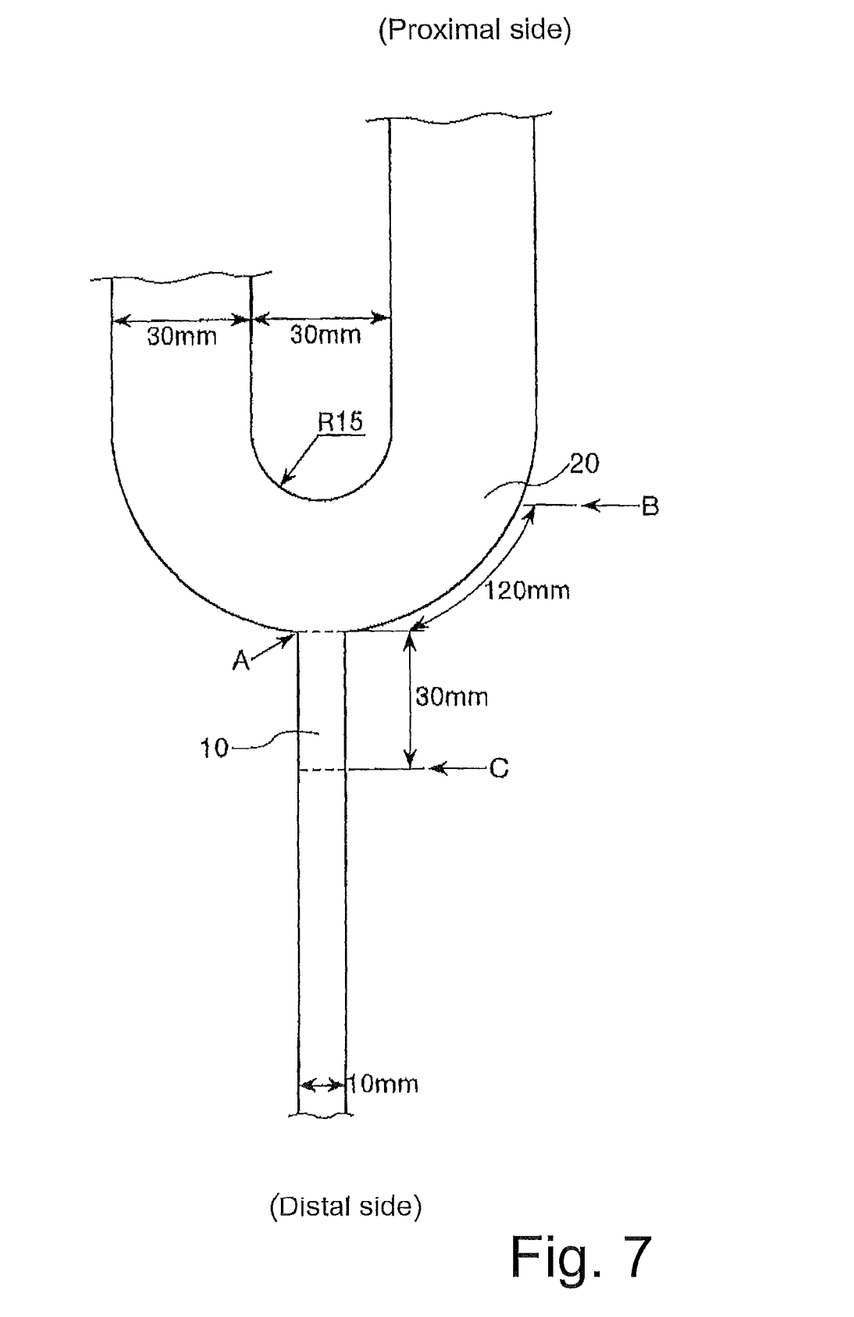
FIG. 7 is a schematic illustration of a carotid artery-aorta model.

In addition, preferably, the catheter assembly 1 has such a transmission characteristic that when a carotid artery-aorta model including a carotid artery 10 (inside diameter: 10 mm) and an aorta 20 (inside diameter: 30 mm) connected to the proximal end of the carotid artery 10, both made of polyvinyl chloride, as shown in FIG. 7 is prepared, the distal end of the outer catheter 2 in the assembled condition is located in the aorta 20 at a position spaced by 120 mm (a position spaced by 120 mm toward the proximal side) along the aorta 20 from a branching point A of the aorta 20 and the carotid artery 10, whereas the distal end of the inner catheter in the assembled condition is located in the carotid artery 10, and the proximal end of the catheter assembly 1 is pushed (moved) in the distal direction by 50 mm at a velocity of 100 mm/min starting from this condition (initial condition), the error ((L1−L2)/L1 100) is not more than 10%, and is particularly in the range of about 2 to 10%, where L1 (50 mm) is the pushing-in distance of the proximal end of the catheter assembly 1, and L2 is the moving distance of the distal end of the inner catheter (the distal end of the soft tip 8). This yields further enhancement of steerability.

The position of the distal end of the inner catheter 6 in the above-mentioned initial condition differs depending on the protrusion length (a) of the inner catheter 6. In the configuration shown in the figure, the distal end of the inner catheter 6 is disposed at position C spaced by 30 mm toward the distal side along the carotid artery 10 from the branching point A.

In addition, the catheter assembly 1 preferably has such a transmission characteristic that when the proximal end of the catheter assembly 1 in the assembled condition is rotated (turned) by a predetermined angle in the circumferential direction in relation to the same carotid artery-aorta model as above and starting from the same condition as above, the error (θ1−θ2) is in the range of 0 to 90° (not more than 90°), particularly about 0 to 60°, where θ1 is the angle by which the proximal end of the catheter assembly 1 is rotated, and θ2 is the angle by which the soft tip 8 is rotated. This results in further enhancement of steerability.

Now, an example of the method of using the catheter assembly 1 will be simply described. A catheter introducer is used to puncture an artery (introduction site), for example a right femoral artery, a right brachial artery or a right radial artery using the Seldinger technique. The catheter assembly 1 with a guide wire inserted in its lumen 77 is inserted into a sheath of the catheter introducer and, while causing the guide wire to precede, a distal portion of the catheter assembly 1 in the assembled condition is inserted into the artery via the tip opening of the sheath.

Next, the catheter assembly 1 is fed forward while the guide wire is moved to precede, and a distal portion of the catheter assembly 1, specifically a distal portion of the inner catheter 6, is gradually advanced toward the carotid artery, which is the site (target site) where a distal portion of the outer catheter 2 is to be inserted and left indwelling. In this case, for smooth passage of the distal portion of the catheter assembly 1 through curved parts (bent parts) of the blood vessels or for appropriate selection of branches of the blood vessels, operations including combinations of insertion and evulsion of the guide wire into and out of the catheter assembly 1, forward and backward movements of the catheter assembly 1 and rotation of the catheter assembly 1 are carried out. The guide wire need not be necessarily be used.

After the arrival of the distal portion of the catheter assembly 1 in the target site, the luer lock connector 91 is then rotated in a predetermined direction, thereby decoupling the hub 9 and the hub 5 from each other. The outer catheter 2 is pushed in and the deformed portion 32 of the outer catheter 2 is engaged with the carotid artery, whereby the outer catheter 2 is immovably fixed in site (in the target site).

Next, the inner catheter 6 is drawn out. Upon drawing-out the inner catheter 6, only the outer catheter 2 is left, with its distal portion (deformed portion 32) in engagement with the carotid artery. In this condition, a blood vessel of the head or neck located on the distal side of the carotid artery is accessible so that a predetermined object can be attained by inserting a treatment catheter via the hub 5 at the proximal portion of the outer catheter 2.

While the catheter assembly disclosed here has been described based on the embodiment shown in the drawing figures, the present invention is not limited to this embodiment, and the configurations of components can be replaced by those of other configurations having functions the same as or equivalent to the functions described above. In addition, other arbitrary structures or features may be added.

As mentioned, the catheter assembly in the above-described embodiment is one used for insertion in a blood vessel of the head or neck. However, the catheter is not necessarily limited in that use.

EXAMPLES

Now, specific working examples will be described below.

Example 1

A catheter assembly (shaped as shown in FIGS. 1-6) provided with an outer catheter and an inner catheter in the following conditions was produced.

[Outer Catheter Body]
Whole length: 1,000 mm
Outside diameter: 2.06 mm
Inside diameter (lumen diameter): 1.80 mm
Length of soft tip: 1 mm
Material of soft tip: Polyester elastomer (Shore hardness=29 D)
Material of inner layer of soft tip: PTFE
Flexural rigidity of soft tip: 6 gf
Length of first part (381): 70 mm
Material of outer layer of first part: Polyester elastomer (Shore hardness=52 D)
Material of inner layer of first part: PTFE
Reinforcing material layer of first part: Braid formed from wire of stainless steel (SUS304WPB) being flat plate-like (35 110 µm) in cross-sectional shape
Flexural rigidity of first part: 36 gf
Length of second part (382): 20 mm
Material of outer layer of second part: Polyester elastomer (Shore hardness=57 D)
Material of inner layer of second part: PTFE
Reinforcing material layer of second part: Braid formed from wire of stainless steel (SUS304WPB) being flat plate-like (35 110 µm) in sectional shape
Flexural rigidity of second part: 47 gf
Length of third part (383): 850 mm
Material of outer layer of third part: Polyester elastomer (Shore hardness=68 D)
Material of inner layer of third part: PTFE
Reinforcing material layer of third part: Braid formed from wire of stainless steel (SUS304WPB) being flat plate-like (35 110 µm) in sectional shape
Flexural rigidity of third part: 56 gf
the flexural rigidity of each part was measured in water at a temperature of 37° C.

[Inner Catheter Body]
Whole length: 1,200 mm
Outside diameter: 1.70 mm
Inside diameter (lumen diameter): 1.22 mm
Length of soft tip: 2 mm
Material of soft tip: Polyurethane elastomer (Shore hardness=85 A)
Flexural rigidity of soft tip: 2.2 gf
Length of flexible section (781): 60 mm
Material of flexible section: Polyurethane elastomer (Shore hardness=53 D)
Flexural rigidity of flexible section: 3.2 gf
Length of first unit physical property transition section 782A): 5 mm
Material of first unit physical property transition section: Polyurethane elastomer (Shore hardness=58 D)
Flexural rigidity of first unit physical property transition section: 4.5 gf
Length of second unit physical property transition section (782A): 5 mm
Material of second unit physical property transition section: Polyurethane elastomer (Shore hardness=62 D)
Flexural rigidity of second unit physical property transition section: 7.0 gf
Length of first body section (783): 80 mm
Material of outer layer of first body section: Polyurethane elastomer (Shore hardness=62 D)
Material of inner layer of first body section: Mixture (polyamide elastomer: polyurethane elastomer=7:3) of polyamide elastomer (Shore hardness=63 D) and polyurethane elastomer (Shore hardness=74 D) (Shore hardness of mixture=70 D)
Flexural rigidity of first body section: 10.4 gf
Protrusion length (b) of second body section from distal end of soft tip of outer catheter: 5 mm
Material of outer layer of second body section: Polyurethane elastomer (Shore hardness=62 D)
Material of inner layer of second body section: Mixture (polyamide elastomer: polyurethane elastomer=7:3) of polyamide elastomer (Shore hardness=63 D) and polyurethane elastomer (Shore hardness=74 D) (Shore hardness of mixture: 70 D)
Reinforcing material layer of second body section: Braid formed from two wires of stainless steel being circular (outside diameter: 50 µm) in sectional shape
Flexural rigidity of second body section: 22.6 gf

Comparative Example 1

A catheter assembly was produced in the same manner as in Example 1, except that in the inner catheter body, no first unit physical property transition section and no second unit physical property transition section were provided, and the length of the first body section was 90 mm.

Comparative Example 2

A catheter assembly (only an outer catheter) was produced in the same manner as in Example 1, except that no inner catheter was provided.

Example 1 and Comparative Examples 1 and 2 are set forth in Table 1 below.

TABLE 1

| | | | Example 1 | | Comp. Ex. 1 | | Comp. Ex. 2 | |
|---|---|---|---|---|---|---|---|---|
| Inner catheter | | Shore hardness | Length (mm) | Flexural rigidity (gf) | Length (mm) | Flexural rigidity (gf) | Length (mm) | Flexural rigidity (gf) |
| Soft tip | Polyurethane elastomer | 85 A | 2 | 2.2 | 2 | 2.2 | Inner catheter is absent | |
| Flexible section | Polyurethane elastomer | 53 D | 60 | 3.2 | 60 | 3.2 | | |
| 1st UPPTS | Polyurethane elastomer | 58 D | 5 | 4.5 | — | — | | |
| 2md UPPTS | Polyurethane elastomer | 62 D | 5 | 7.0 | — | — | | |
| 1st body section | Outer layer/Inner layer | Outer layer 62 D Inner layer 70 D | 80 | 10.4 | 90 | 10.4 | | |
| 2nd body section | Outer layer/Inner layer + RML | Outer layer 62 D Inner layer 70 D | 5* | 22.6 | 5* | 22.6 | | |
| Outer catheter | | Shore hardness of resin | Length (mm) | Flexural rigidity (gf) | Length (mm) | Flexural rigidity (gf) | Length (mm) | Flexural rigidity (gf) |
| Soft tip | Polyester elastomer + Inner layer PTFE | 29 D | 1 | 6 | 1 | 6 | 1 | 6 |
| 1st part | Polyester elastomer + RML + Inner layer PTFE | 52 D | 70 | 36 | 70 | 36 | 70 | 36 |
| 2nd part | Polyester elastomer + RML + Inner layer PTFE | 57 D | 20 | 47 | 20 | 47 | 20 | 47 |
| 3rd part | Polyester elastomer + RML + Inner layer PTFE | 68 D | 850 | 56 | 850 | 56 | 850 | 56 |

Notes:
UPPTS = Unit physical property section
RML = Reinforcing material layer
*= Protrusion length from distal end of outer catheter <Evaluation (Transmission Characteristic, Resistance)>

By use of the carotid artery-aorta model including polyvinyl chloride tubes shown in FIG. 7 in water at a temperature of 37° C., the transmission characteristic of the catheter assembly of Example 1 was evaluated. The carotid artery-aorta model used includes a carotid artery 10 having an inside diameter of 10 mm, and an aorta 20 connected to the proximal end of the carotid artery 10 and having an inside diameter of 30 mm. The aorta 20 has a curved part so curved that the radius of curvature on the inner side is 15 mm (the gap distance between the aorta portions is 30 mm), and the carotid artery 10 extends in a direction substantially perpendicular to the curved part of the aorta 20.

Figure 8:
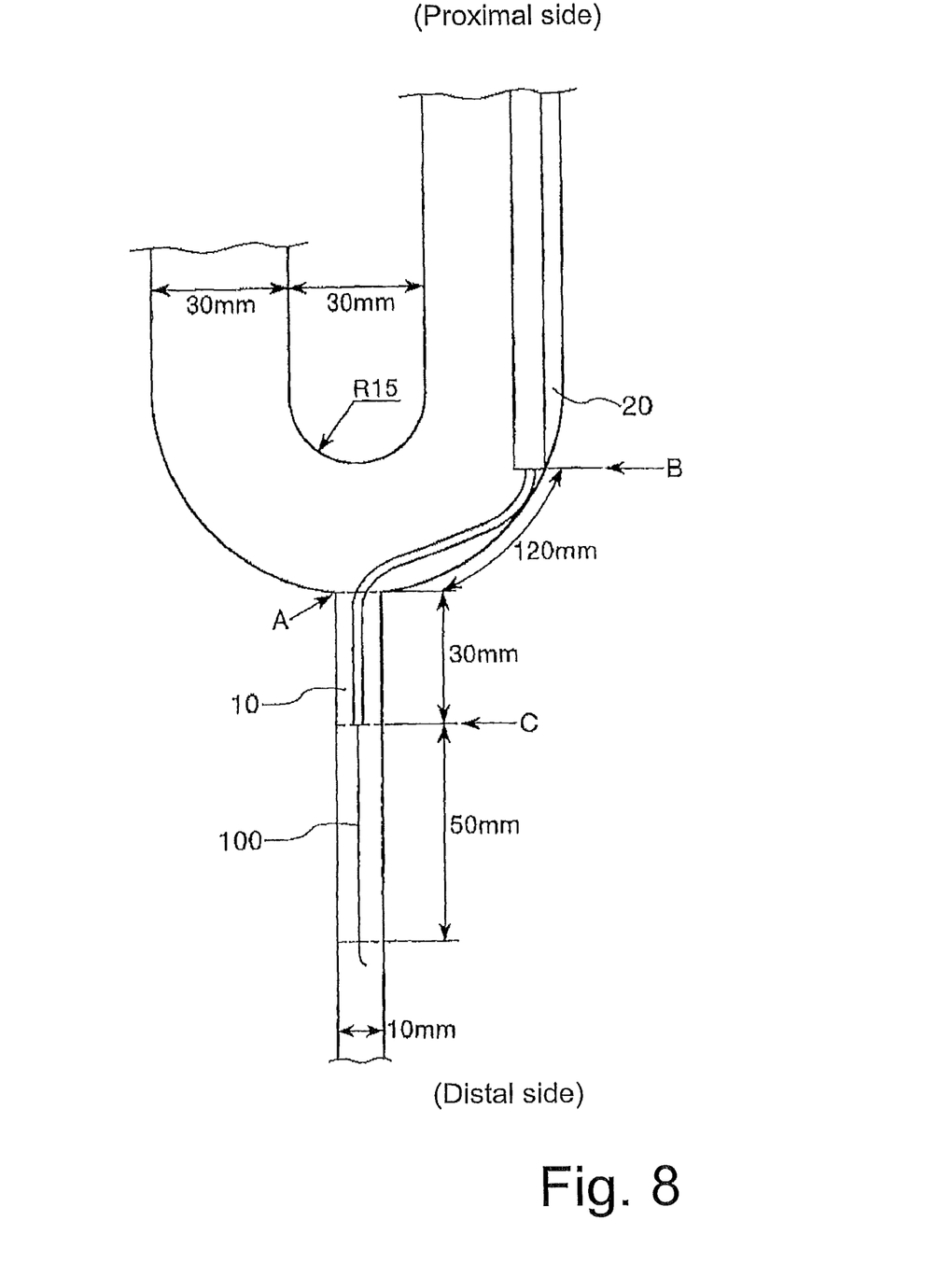
FIG. 8 is a schematic illustration similar to FIG. 7 illustrating the condition in which evaluation is carried out using the carotid artery-aorta model.

First, as shown in FIG. 8, the distal end of the inner catheter of the catheter assembly inserted from the heart side (proximal side) of the aorta 20 of the carotid artery-aorta model was advanced along the guide wire 100 through the aorta 20 to the branching point A of the aorta 20 and the carotid artery 10.

Next, the distal end of the inner catheter of the catheter assembly was advanced into the carotid artery 10, and extended from the branching point A toward the head side (peripheral side) (distal side) of the carotid artery 10. In this instance, the distal end of the outer catheter of the catheter assembly was disposed at position B (in the aorta 20) spaced by 120 mm toward the heart side from the branching point A (this disposition is expressed as −120 mm). Simultaneously, the distal end of the inner catheter of the catheter assembly was disposed at position C (in the carotid artery 10) spaced by 30 mm toward the peripheral side (distal side) from the branching point A (this disposition is expressed as +30 mm).

Starting from this condition, the proximal end of the catheter assembly was pushed in and it was advanced by 50 mm along the distal direction at a velocity of 100 mm/min. The maximum resistance during this movement was measured by an autograph. In addition, the moving distance of the distal end of the inner catheter of the catheter assembly was measured.

Besides, for the catheter assembly (the outer catheter and the inner catheter) of Comparative Example 1, the maximum resistance and the moving distance of the distal end of the inner catheter of the catheter assembly were measured in the same manner as for the catheter assembly of Example 1.

In addition, as for the catheter assembly (the inner catheter was absent and only the outer catheter was present) of Comparative Example 2, the distal end of the outer catheter was disposed at position C (in the carotid artery 10) spaced by 30 mm toward the peripheral side (distal side) from the branching point A (this disposition is expressed as +30 mm), and, starting from this condition, the proximal end of the catheter assembly was pushed in and it was advanced by 50 mm along the distal direction at a velocity of 100 mm/min. During this movement, the maximum resistance and the moving distance of the distal end of the outer catheter of the catheter assembly were measured.

These results are shown in Table 2 below.

TABLE 2

|  | Position of distal end of outer catheter from branching point A (mm) | Position of distal end of inner catheter from branching point A (mm) | Protrusion length (a) of Inner catheter (mm) | Maximum resistance (gf) | Moving distance of distal end (mm) |
|---|---|---|---|---|---|
| Example 1 | −120 | 30 | 150 | 50 | 49 |
| Comparative Example 1 | −120 | 30 | 150 | 75 | 40 |
| Comparative Example 2 | 30 | — | — | 72 | 25 |

In the case of the catheter assembly of Example 1, the distal end (the distal end of the catheter assembly) was moved by 49 mm when the proximal end (the proximal end of the catheter assembly) was pushed in by 50 mm. On the other hand, in the case of the catheter assembly of Comparative Example 1, the corresponding movement of the distal end was only 40 mm. It is seen that the error in transmission characteristic between the proximal end to the distal end of the catheter assembly of Example 1 is 2%, a very small value. Incidentally, in the case of the catheter assembly of Comparative Example 2, the distal end was moved by only 25 mm.

Besides, the maximum resistance during when the catheter assembly of Example 1 was pushed in was 50 gf. On the other hand, for the catheter assembly of Comparative Example 1, the corresponding maximum resistance was 75 gf. It is seen that in the case of the catheter assembly of Example 1, the pushing-in resistance is small. In addition, the pushing-in distance of the proximal end and the moving distance of the distal end are roughly equal to each other. This shows that the damage of the blood vessel by the catheter is little, and the catheter can be safely fed into a target region. Incidentally, for the catheter assembly of Comparative Example 2, the maximum resistance was 72 gf.

From the foregoing, it has been verified that the catheter assembly according to the present invention is suitable as a catheter in terms of entrance into the carotid artery.

The present invention may be practiced or embodied in still other ways without departing from the spirit or essentials thereof. The preferred embodiment described herein is therefore illustrative and not restrictive, the scope of the invention being indicated by the appended claims and all variations which come within the meaning of the claims are intended to be embraced therein.

What is claimed is:

1. A catheter assembly used for treatment of a blood vessel of the head or neck, said catheter assembly comprising:
    an outer catheter comprised of an outer catheter body and an outer catheter hub at a proximal portion of the outer catheter body;
    an inner catheter comprised of: an inner catheter body possessing an outer circumference configured to allow the inner catheter body to be positioned inside the outer catheter body; a tip at a distal-most portion of the inner catheter body, the tip being softer that the distal portion of the inner catheter body; and an inner catheter hub at a proximal portion of the inner catheter body and configured to be coupled to the outer catheter hub in a coupled condition by way of a lock which holds the inner and outer catheter bodies in a coupled condition;
    the inner catheter body comprising:
        a flexible section having a distal end to which is fixed the tip;
        a physical property transition section on a proximal side of the flexible section;
        a first body section on the proximal side of the physical property transition section,
        a second body section on the proximal side of the first body section;
        the second body section possessing a flexural rigidity greater than the flexural rigidity of the first body section;
        the second body section comprising a reinforcing material layer embedded in material of which the second body section is made, and the reinforcing material layer being made of a material different from the material of which the second body section is made;
        relationships of $1<\sigma_{2X}/\sigma_1 \leqq 2$ and $1<\sigma_3/\sigma_{2Y} \leqq 2$ are satisfied, where $\sigma_1$ [gf] is the flexural rigidity of the flexible section of the inner catheter body in water at a temperature of 37° C., $\sigma_{2X}$ [gf] is the flexural rigidity of a distal portion of the physical property transition section, $\sigma_{2Y}$ [gf] is the flexural rigidity of a proximal portion of the physical property transition section, and $\sigma_3$ [gf] is the flexural rigidity of the first body section;
    the inner catheter and the outer catheter each possessing a length such that with the inner catheter positioned inside the outer catheter and the outer catheter hub and the inner catheter hub coupled to each other in the coupled condition by the lock, a distal portion of the second body section protrudes distally beyond a distal-most end of the outer catheter body;
    wherein said first body section, said physical property transition section, said flexible section and said tip are distal to said distal portion of the second body section, whereby said first body section, said physical property transition section, said flexible section and said tip also protrude distally beyond a distal-most end of the outer catheter body; and
    the flexural rigidity of a distal portion of the outer catheter body is higher than the flexural rigidity of the second body section.

2. The catheter assembly according to claim 1, wherein the reinforcing material layer is a spirally wound wire, and the flexible section, the physical property transition section and the first body section are devoid of any spirally wound wire.

3. The catheter assembly according to claim 1, wherein the first and second body sections each comprise an inner layer and an outer layer comprised of different material compositions, the material composition of the inner layer in the first and second body sections being the same, the material composition of the outer layer in the first and second body sections being the same.

4. The catheter assembly according to claim 1, wherein said second body section has a flexural rigidity of 22.6 gf, said first body section has a flexural rigidity of 10.4, said proximal portion of the physical property transition section has a flexural rigidity of 7.0 gf, said distal portion of the physical property transition section has a flexural rigidity of 4.5 gf, said flexible section has a flexural rigidity of 3.2 gf, and said tip has a flexural rigidity of 2.2 gf.

5. The catheter assembly according to claim 1, wherein said proximal portion of the physical property transition section has a Shore hardness of 62 D, said distal portion of the physical property transition section has a Shore hardness of 62 D, said flexible section has a Shore hardness of 53 D, and said tip has a Shore hardness of 85 A.

6. The catheter assembly according to claim 1, wherein a portion of the inner catheter protruding distally beyond the distal-most end of the outer catheter body has a length of 157 mm.

7. A catheter assembly used for treatment of a blood vessel of the head or neck, said catheter assembly comprising:
 an outer catheter comprised of an outer catheter body and an outer catheter hub at a proximal portion of the outer catheter body;
 an inner catheter comprised of: an inner catheter body possessing an outer circumference configured to allow the inner catheter body to be positioned inside the outer catheter body; a tip at a distal-most portion of the inner catheter body, the tip being softer that the distal portion of the inner catheter body; and an inner catheter hub at a proximal portion of the inner catheter body and configured to be coupled to the outer catheter hub in a coupled condition by way of a lock which holds the inner and outer catheter bodies in a coupled condition;
 the inner catheter body comprising:
  a flexible section having a distal end to which is fixed the tip;
  a physical property transition section on a proximal side of the flexible section;
  a first body section on the proximal side of the physical property transition section,
  a second body section on the proximal side of the first body section;
  the second body section possessing a flexural rigidity greater than the flexural rigidity of the first body section;
  the second body section comprising a reinforcing material layer embedded in material of which the second body section is made, and the reinforcing material layer being made of a material different from the material of which the second body section is made;
  relationships of $1<\sigma_{2X}/\sigma_1 \leq 2$ and $1<\sigma_3/\sigma_{2Y} \leq 2$ are satisfied where $\sigma_1$ [gf] is the flexural rigidity of the flexible section of the inner catheter body in water at a temperature of 37° C., $\sigma_{2X}$ [gf] is the flexural rigidity of a distal portion of the physical property transition section, $\sigma_{2Y}$ [gf] if is the flexural rigidity of a proximal portion of the physical property transition section, and $\sigma_3$ [gf] is the flexural rigidity of the first boy section;
 the inner catheter and the outer catheter each possessing a length such that with the inner catheter positioned inside the outer catheter and the outer catheter hub and the inner catheter hub coupled to each other in the coupled condition by the lock, a distal portion of the second body section protrudes distally beyond a distal-most end of the outer catheter body; and
 the flexural rigidity of a distal portion of the outer catheter body is higher than the flexural rigidity of the second body section;
 wherein a portion of the inner catheter protruding distally beyond the distal-most end of the outer catheter body has a length of 157 mm; and
 wherein said second body section has a length of 5 mm protruding beyond the distal-most end of the outer catheter body, said first body section has a length of 80 mm, said proximal portion of the physical property transition section has a length of 5 mm, said distal portion of the physical property transition section has a length of 5 mm, said flexible section has a length of 60 mm, and said tip has a length of 2 mm.

8. The catheter assembly according to claim 7, wherein the reinforcing material layer is a spirally wound wire, and the flexible section, the physical property transition section and the first body section are devoid of any spirally wound wire.

9. The catheter assembly according to claim 7, wherein the first and second body sections each comprise an inner layer and an outer layer comprised of different material compositions, the material composition of the inner layer in the first and second body sections being the same, the material composition of the outer layer in the first and second body sections being the same.

10. The catheter assembly according to claim 7, wherein said second body section has a flexural rigidity of 22.6 gf, said first body section has a flexural rigidity of 10.4, said proximal portion of the physical property transition section has a flexural rigidity of 7.0 gf, said distal portion of the physical property transition section has a flexural rigidity of 4.5 gf, said flexible section has a flexural rigidity of 3.2 gf, and said tip has a flexural rigidity of 2.2 gf.

11. The catheter assembly according to claim 7, wherein said proximal portion of the physical property transition section has a Shore hardness of 62 D, said distal portion of the physical property transition section has a Shore hardness of 62 D, said flexible section has a Shore hardness of 53 D, and said tip has a Shore hardness of 85 A.

* * * * *